US008028696B2

(12) United States Patent
Juergensen

(10) Patent No.: US 8,028,696 B2

(45) Date of Patent: *Oct. 4, 2011

(54) DISPLAY INTEGRATED VIBRATING ALARM

(76) Inventor: Kevin Juergensen, Addison, PA (US)

( * ) Notice: Subject to any disclaimer, the term of this patent is extended or adjusted under 35 U.S.C. 154(b) by 105 days.

This patent is subject to a terminal disclaimer.

(21) Appl. No.: 12/607,795

(22) Filed: Oct. 28, 2009

(65) Prior Publication Data

US 2010/0188214 A1 Jul. 29, 2010

Related U.S. Application Data

(63) Continuation of application No. 11/067,175, filed on Feb. 25, 2005, now Pat. No. 7,628,153.

(51) Int. Cl.
*A61M 11/00* (2006.01)

(52) U.S. Cl. ................... 128/204.26; 128/202.22; 116/3

(58) Field of Classification Search ............. 128/204.19, 128/204.21, 204.22, 204.26; 367/134, 116; 116/3, DIG. 17
See application file for complete search history.

(56) References Cited

U.S. PATENT DOCUMENTS

| | | | | |
|---|---|---|---|---|
| 3,037,501 | A | 6/1962 | Miller | |
| 4,470,413 | A | 9/1984 | Warncke | |
| 5,381,801 | A * | 1/1995 | McShane et al. | 128/848 |
| 6,401,714 | B1 | 6/2002 | Giorgini | |
| 6,519,548 | B1 * | 2/2003 | Kuroda et al. | 702/139 |
| 6,856,578 | B2 | 2/2005 | Magine et al. | |
| 7,628,153 | B2 | 12/2009 | Juergensen | |
| 2002/0176323 | A1 | 11/2002 | Magine et al. | |
| 2004/0223876 | A1 | 11/2004 | Kirollos et al. | |

* cited by examiner

*Primary Examiner* — Steven Douglas
(74) *Attorney, Agent, or Firm* — Powley & Gibson, P.C.

(57) ABSTRACT

An alarm system and method for use with a breathing apparatus that provides a source of breathable air to a user/diver. A tactile signal is generated in response to a signal representing at least one parameter corresponding to the breathing apparatus status, and the tactile signal can be both felt and heard by the user. The tactile signal may be generated in combination with a visual and/or an additional audible alarm. The tactile signal may be a vibration. The alarm may be worn on the face, either on the mask or on the mouthpiece. The vibrator serves two functions, one as a tactile alarm that the diver can feel during operation, and a second as an auditory alarm through bone-conduction of sound. The tactile alarm indicates to the user/diver that his particular unit is the one transmitting an alarm signal, and cannot be mistaken for any other device. The tactile signal may be generated to have one or more signal characteristics that are modulated to convey additional information about the parameter or parameters being monitored.

30 Claims, 7 Drawing Sheets

DISPLAY INTEGRATED VIBRATING ALARM

CROSS-REFERENCE TO RELATED APPLICATIONS

The present application is a continuation of my application Ser. No. 11/067,175, filed Feb. 25, 2005, which is incorporated herein by reference in its entirety.

FIELD OF THE INVENTION

The present invention relates to an underwater breathing apparatus, and, more particularly, to the provision of alert systems to monitor diving parameters, including breathing gas status.

BACKGROUND OF THE INVENTION

In Closed Circuit Mixed Gas Diving and/or other SCUBA diving applications, wherein a diver is breathing different levels of oxygen, nitrogen, helium and sometimes carbon dioxide, it becomes important that a diver be notified of certain dangerous conditions in the breathing gas or when the amount of a breathing gas is low. In the prior art, divers typically monitor levels and amounts of gas by meters, gauges and electronic displays that are secured to a diver and audible alarms. The prior art also employs light systems, which can be seen by a diver while breathing the gas of a system and provide a visual warning.

The meter, gauges and display systems mounted on the arm or other area on the diver do not effectively alert the diver to dangerous conditions, since they cannot be constantly monitored by the diver.

One problem with alert systems found in the prior art that feature only a light notification, such as a flashing bulb or activation of a LED, is that it can be obscured by other bright lights from another diver or the sun in shallow or clear water.

Auditory ("beeper") type alarms have been used in numerous diving systems for years. The disadvantage to such systems is that often circumstances are such that an individual diver cannot hear the alarm, or mistakes others alarms for his own, or vice-versa, resulting in the diver ignoring the alarm he hears.

In the prior art, most underwater alarm systems utilized audible alarms to indicate problems that the individual diver has with his system. These alarms could often be unheard (due to various factors, such as external hoods being wont by the diver) and were often mistaken for other alarms being transmitted by other diver's units in a group diving situation, resulting in confusion. Vibrating alarms have also been used in similar applications with similar shortcomings.

SUMMARY OF THE INVENTION

The foregoing and other problems and deficiencies in known diving monitor and alarm systems are solved and a technical advance is achieved by the display integrated vibrating alarm system of the present invention.

In accordance with an aspect of the present invention, there is provided an alarm apparatus for use with a breathing apparatus that provides a source of breathable air to a user, and the alarm apparatus comprises a tactile signal generator that is selectively energized in response to a signal representing at least one parameter corresponding to the breathing apparatus status to generate a tactile signal that is capable of being felt and heard by the user wearing the alarm apparatus. The tactile signal may be a vibration, and such vibration may be generated by a motor that rotates an eccentric weight. The user wearing the alarm apparatus feels the tactile signal stimulating nerve endings in the skin, deep tissue, teeth, and/or skeletal bones, joints. The user wearing the alarm also hears the tactile signal, as the tactile signal also couples into the bone structure to stimulate the user's/diver's auditory system (i.e., acoustic energy coupled into the bone structure reaches and stimulates the diver's Cochlea).

One or more parameters corresponding to the breathing apparatus may include at least one status condition for the breathing gas, such as, for example, one or more of the following: at least one of an amount, level, and partial pressure of at least one component in the breathing gas; and/or an amount, level, and pressure of gas in tanks or containers supplying the breathing gas to the diver.

In accordance with another aspect of the present invention, the alarm apparatus includes a light emitting device responsive to the same and/or a different signal representing at least one parameter corresponding to the breathing apparatus status. The light emitting device and the tactile signal generator may be both energized at substantially the same time to provide a visual signal and a tactile signal to the user. Alternatively, the tactile signal generator may be energized at a time delay after the light emitting device is energized in the event that the light emitting device remains energized for a predetermined period of time (e.g., the light emitting device remaining energized indicating that the alarm condition persists and thus the user should be further alerted by a tactile signal).

In accordance with yet a further aspect of the present invention, a signal to which the tactile generator is responsive and/or a signal to which a light emitting device is responsive (which, in some implementations, may be the same signal) may be coupled (e.g., directly connected or indirectly (e.g., via circuitry) connected) to the output of at least one sensor. Additionally, or alternatively, such a signal may be provided by a dive computer and corresponds to dive computer data.

In accordance with a further aspect of the present invention, a tactile signal is generated to have one or more signal characteristics that are modulated to convey additional information about the parameter or parameters being monitored. Signal characteristics that may be modulated include frequency, intensity, duration, repetition frequency, and pattern. Differently modulated signals may represent, for example, different parameters, different warning levels for a given parameter, and/or quantitative information about a given parameter.

In accordance with an aspect of the present invention, a tactile alarm, preferably in combination with a visual and/or audible alarm, is provided which indicate to the diver that his particular unit was the one transmitting an alarm signal, and could not be mistaken for any other device. Further, since the alarm can be designed to be worn on the face, either on the mask or on the mouthpiece, the vibrator serves two functions, one as a tactile alarm that the diver can feel during operation, but also through bone-conduction of sound, as an auditory alarm as well.

As will be appreciated in view of the foregoing and the ensuing description, an illustrative, non-exclusive, and non-limiting feature of the present invention is that a tactile alarm generated in accordance therewith cannot be easily ignored, overlooked or confused as to source, thus eliminating the possibility of mistaking the alarm for that of another user/diver by providing a personal tactile sensation to the individual user/diver who is wearing the system.

DESCRIPTION OF THE DRAWING

The foregoing and other features and advantages of the present invention will become more apparent in light of the following detailed description of exemplary embodiments thereof, as illustrated in the accompanying drawings, where.

DETAILED DESCRIPTION

Display Integrated Vibration Alarm (DIVA™), which refers to an embodiment of the present invention, provides an improved alarm and motoring system which can monitor Oxygen Levels during Closed Circuit Mixed Gas Diving Operations (such as, e.g., SCUBA) and provide both visual and tactile cues to the user. Among the DIVA™'s functionality, the unit can visually display or indicate the status of a diver's breathing Loop Oxygen Content as displayed in Partial Pressure, as well as alert the diver if the Oxygen Levels in his breathing gas fall above or below thresholds that are considered dangerous. A vibrating portion of the DIVA™ device allows for tactile cues to make the diver-user aware of any potentially dangerous condition of his breathing gas mixture due to the device's being mounted on the diver's mask or mouthpiece (so as to allow translation of any vibrating motion caused by the vibrating portion of the device to the diver himself). Preferably, the vibrations also couple into the bone structure to stimulate the diver's auditory system (i.e., acoustic energy coupled into the bone structure reaches and stimulates the diver's cochlea).

Figure 1:
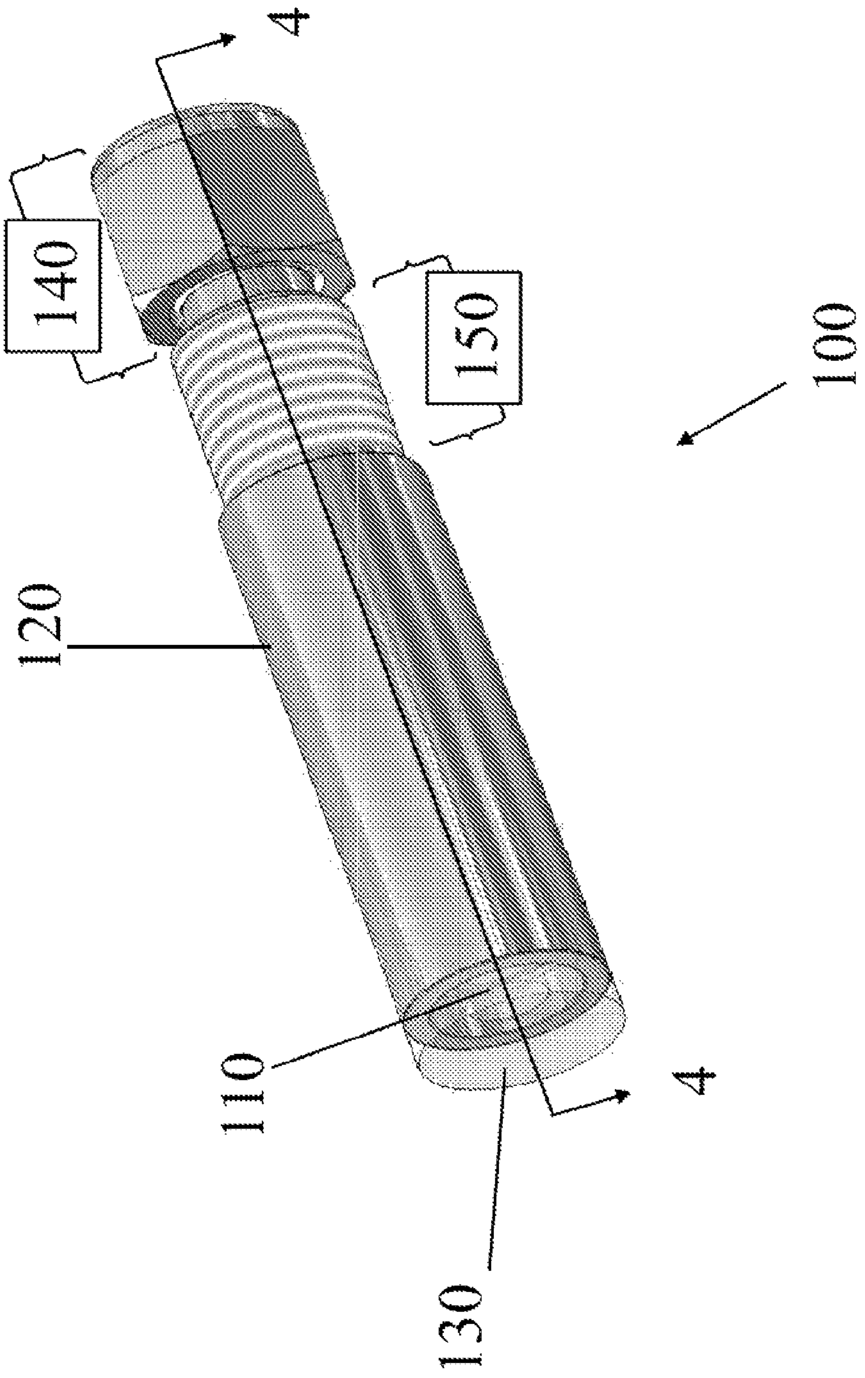
FIG. 1 is a display integrated vibrating alarm (DIVA™) system according to an illustrative embodiment of the present invention.

With reference to FIG. 1, an illustrative embodiment of the display integrated vibration alarm (DIVA™) system of the present invention is shown. This embodiment of the DIVA™ is adapted to use for closed circuit rebreather (“CCR”) system applications.

The illustrative DIVA™ 100 comprises a housing 120, which in this embodiment, is chosen to be a stainless steel cylinder. A removable end cap 140 is disposed on a proximal end of the cylinder with a translucent or transparent cap 130 sealing the distal end of the cylinder. Visible behind the cap 130 is a light emitting device 110, which in this embodiment is implemented as a light emitting diode (LED) device. In this illustrative embodiment, threaded portion 150, provides a mechanism to removably secure end cap 140 to cylinder 120. In this configuration, the system does not allow the intrusion of water such that the system is sealed from the environment. End cap 140 is a nut/cap of a Swagelok fitting (or the like) which allows for a sealed connection of cable or conduit to DIVA™ 100.

Figure 2:
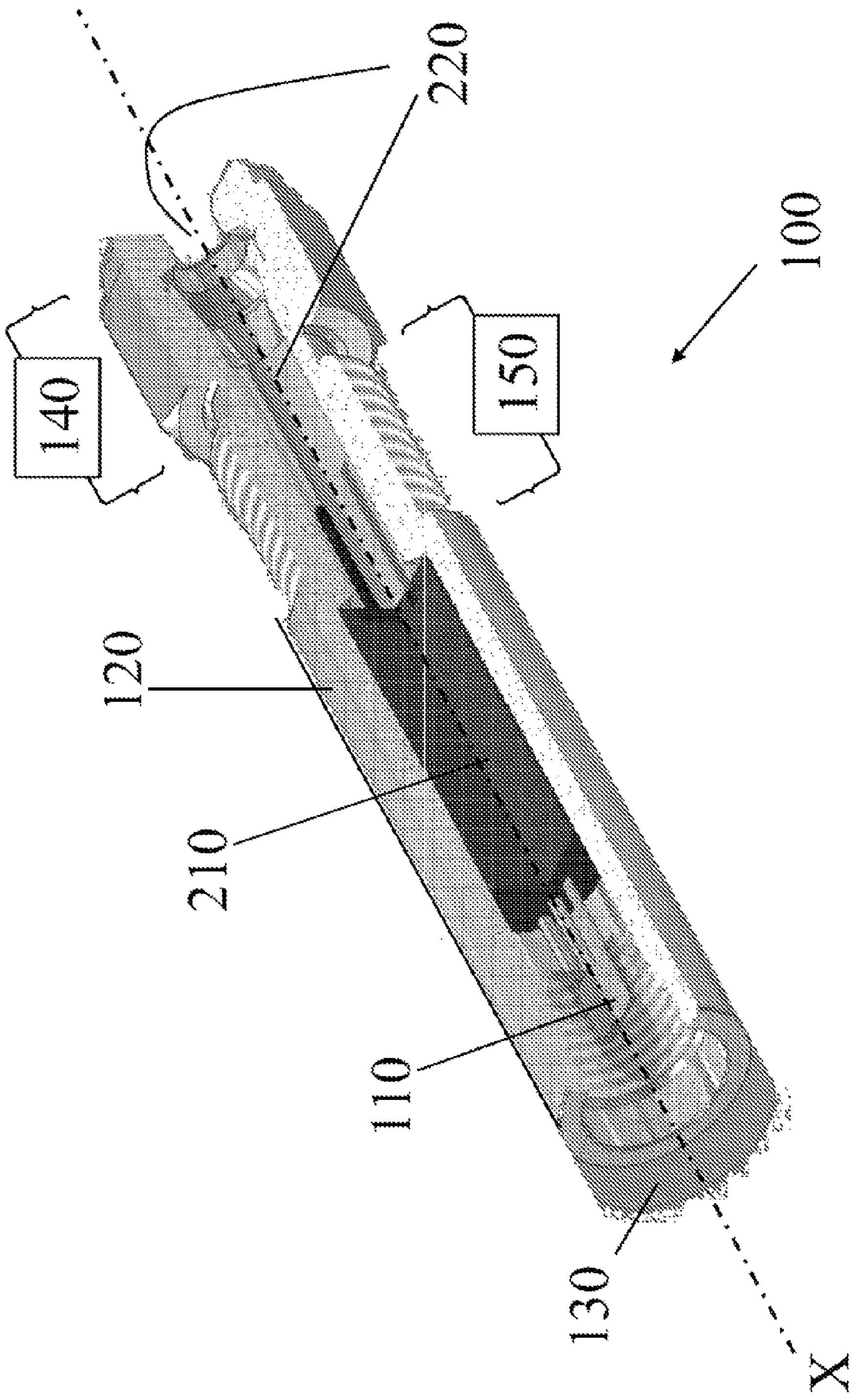
FIG. 2 is a cutaway view of the DIVA™ of FIG. 1.

In FIG. 2, a cutaway view of the DIVA™ 100 of FIG. 1 is shown, to reveal the inside of the DIVA™. A vibration generator 210 is provided, disposed within the housing 120, and in this embodiment, behind (along the longitudinal axis X of the DIVA™ 100) the LED. In the illustrative embodiment, the vibration generator is a Sealed Vibrating Motor 210, which, when activated, spins an eccentric weight at approximately 7,000 rpm. The vibration generator 210 in the DIVA™ can thus provide a tactile cue to the diver, and can also provide an audible cue if the vibrations are coupled to the diver. For instance, when deployed such that it is mounted to the diver's mask or mouthpiece, the DIVA™ will not only transmit pulses of vibration to the diver's head (via conduction to the bone of the diver's head (e.g., jaw and/or skull)), but also perceivable sound is created—thus the diver feels and hears his alarms at the same time, eliminating a disorienting situation occurring in know systems that where a diver is unsure if a particular alarm is his or that of a fellow diver.

The vibrating motor 210 is preferably connected to one or more sensors (not shown) via connection through accessway 220. (See, e.g., conduit 600 shown in FIG. 7) When a sensor detects a predetermined alarm condition, for e.g., a certain amount, level and/or partial pressure of one or more components in the breathing gas, such as, oxygen, helium, nitrogen or carbon dioxide, it sends an electronic signal to the vibrating motor in the housing to activate the motor, thus alerting the diver as discussed above.

The sensor triggered alarm can also be activated by sensors which detect a certain pressure or amount of gas in the tanks or containers supplying the breathing gas to the diver. In an alternative embodiment, the diver can program a (dive) computer or other electronic device to vary the levels of gas and/or type of gas which activates the motor—i.e., the alarm thresholds are settable by the user.

In accordance with a further implementation of the present invention, the vibration signal may be generated to have one or more signal characteristics that are modulated to convey additional information about the parameter or parameters being monitored. Signal characteristics that may be modulated include, for example, frequency, intensity, duration, repetition frequency, and pattern. Differently modulated signals may represent, for example, different parameters, different warning levels for a given parameter, and/or quantitative information about a given parameter. Parameter levels/amounts that trigger the vibration signal, as well as the vibration signal characteristics (e.g., pattern, repetition frequency, etc.) may be user programmable or otherwise user settable.

By way of example, two parameters that may be monitored by DIVA™ are the amount of air remaining in the tank, and the partial pressure of oxygen. If the amount of air remaining in the tank becomes lower than a first predetermined amount, then a one-second pulse may be generated approximately every minute. As the air remaining in the tank drops below one or more predetermined lower levels, then a one-second pulse would be repeated at correspondingly higher repetition rates.

Similarly, the oxygen partial pressure level may be represented by a pattern of two one-third second vibration pulses separated by a short delay (e.g., one-third second), and the repetition frequency of this pattern may be increased as the oxygen partial pressure becomes increasingly dangerous. Alternatively, for example, the pattern of vibration pulses may indicate the partial pressure of oxygen, and the pattern may be repeated at fixed time intervals or at a time interval that depends on the criticality of the oxygen partial pressure level. For instance, two vibration pulses per pattern may indicate a safe level, three pulses per pattern a less safe level, etc.

Alternatively, the number of pulses per pattern and/or the pattern itself may be more specifically mapped to oxygen partial pressure quantities, at least over a range of oxygen partial pressure values. For instance, over the range of 0.4 to 0.8 atm, a partial pressure amount may be quantized/rounded in 0.2 increments and represented as a number of consecutive one-third second pulses, separated by a one-third second delay, with each pulse representing 0.2 atm. Thus, 0.4 atm would be represented by two consecutive one-third second pulses. Over the range of 1.0 to 1.8 atm, the partial pressure amount may be quantized/rounded in 0.2 increments and represented as a two-third second vibration pulse (representing 1.0) followed by a number of consecutive one-third second pulses each representing 0.2 atm, with a one-third second delay between each vibration pulse in the pattern. Thus, a 1.2 concentration would be signaled as a two-thirds of a second pulse followed by a single one-third second pulse. Oxygen concentration amounts above or below this range may be signaled by a common warning, such as a continuous vibration or a continuous one-third second vibration/one-third second delay pulse train. In this way, the oxygen partial pressure quantity over the range of 0.4 to 1.8, quantized/rounded in 0.2 atm increments, is conveyed to the user through the vibrations. The repetition rate of these patterns may be increased for more dangerous quantities (i.e., approaching hypoxic or hyperoxic levels).

As may be appreciated, in this way, the user recognizes the one-second vibration pulse as signaling the amount of air remaining in the tank, and the shorter vibration pulse pattern (i.e., having one-third second and possibly two-third second pulses) as signaling the oxygen partial pressure, with the pulse/pattern repetition frequency and/or the pattern as corresponding to the amounts of these monitored parameters.

While independently deployable, in the illustrative embodiment, the vibrating alarm is combined with a visual indicator, which in the illustrative case is a three color LED 11 that can transmit light of three different colors, red, green, or red/green, which together yields orange. The three-color LED allows conveyance of more information by a combination of colors, in contrast to a more limited array of alarms which would be available with a single color LED. The LED can be programmed to provide various levels of alert or other status conditions in the diver's breathing gas, such as low gas levels, low tank pressure, or different concentrations or partial pressures of specific components of the breathing gas. The DIVA™ can be worn by a scuba diver on their diving mask or breathing mouthpiece such that the distal end of the housing 120, through which the LED 110 is visible, is positioned so it can be viewed by the diver. The DIVA™ is mounted such that the LED 110 is positioned directly in the diver's field of vision.

The LED and vibration motor can be programmed to trigger at the same threshold or their triggering can be offset or staggered.

All DIVA™ Alarms/Notifications thresholds and settings are software adjustable/settable. The DIVA™ Alarms include:

Low/High Set-Point out-of-range (On/Off)
Fast Ascent Warning (On/Off)
Deco Stop Violation Warning (On/Off)
Hypoxic Mix Alarm (On/Off)

Figure 3:
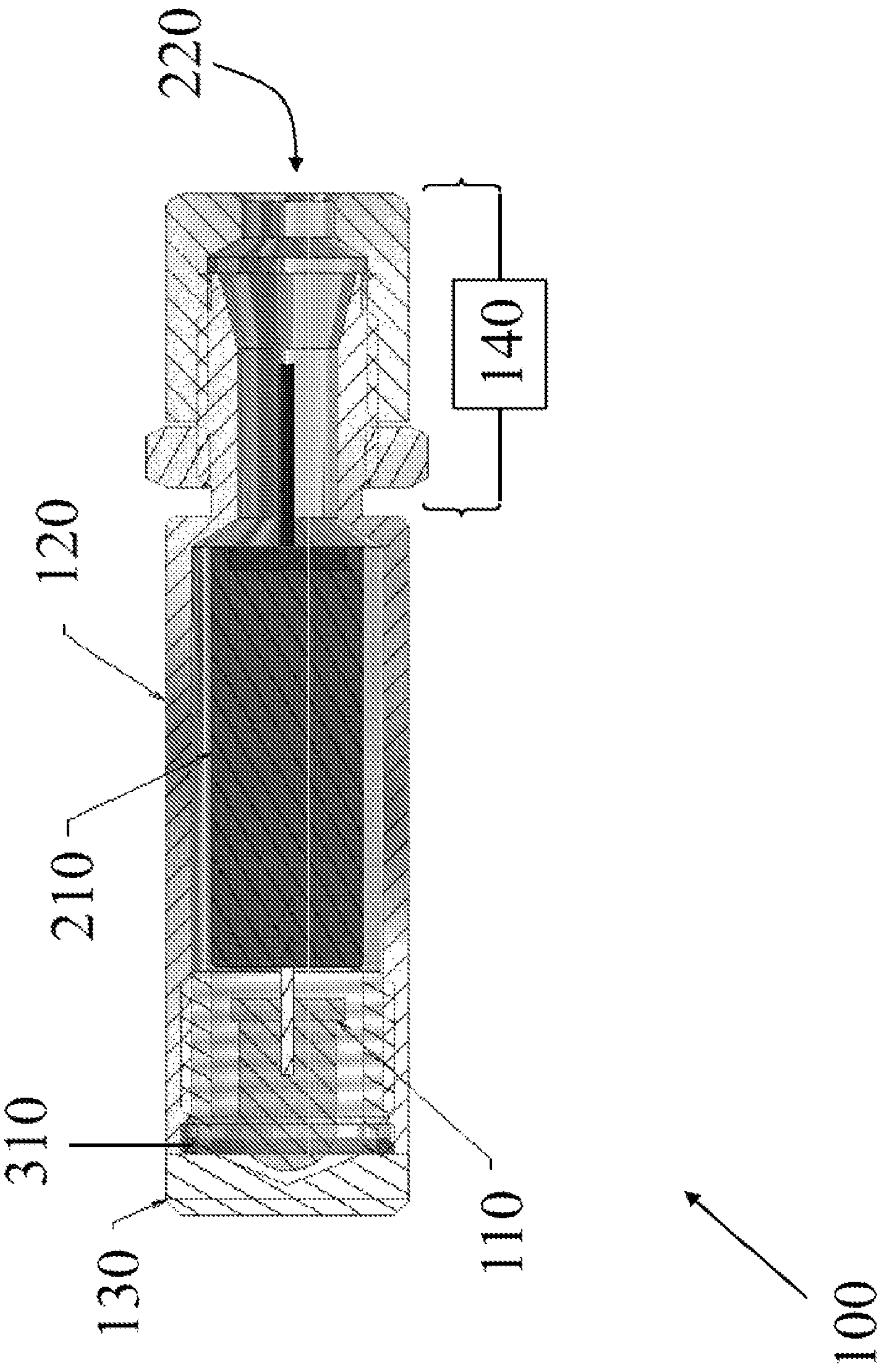
FIG. 3 is a sectional view of the DIVA™ of FIG. 1, shown at section 4-4 (FIG. 1)

As shown in FIG. 3, cap 130 is used to seal the distal end of the housing 120. In the illustrative embodiment the cap is a mushroom-shaped, optically passive cap, which simply allows light from the LED to exit the housing. In the illustrative embodiment, the cap 130 is formed as a convex lens for enhancing focusing of emissions of the LED in the diver's field of vision. At the distal end of the housing 120, an o-ring 310 removably retains and seals cap 130, which is the form of a "mushroom" in a fashion mated to the housing.

Figure 4:
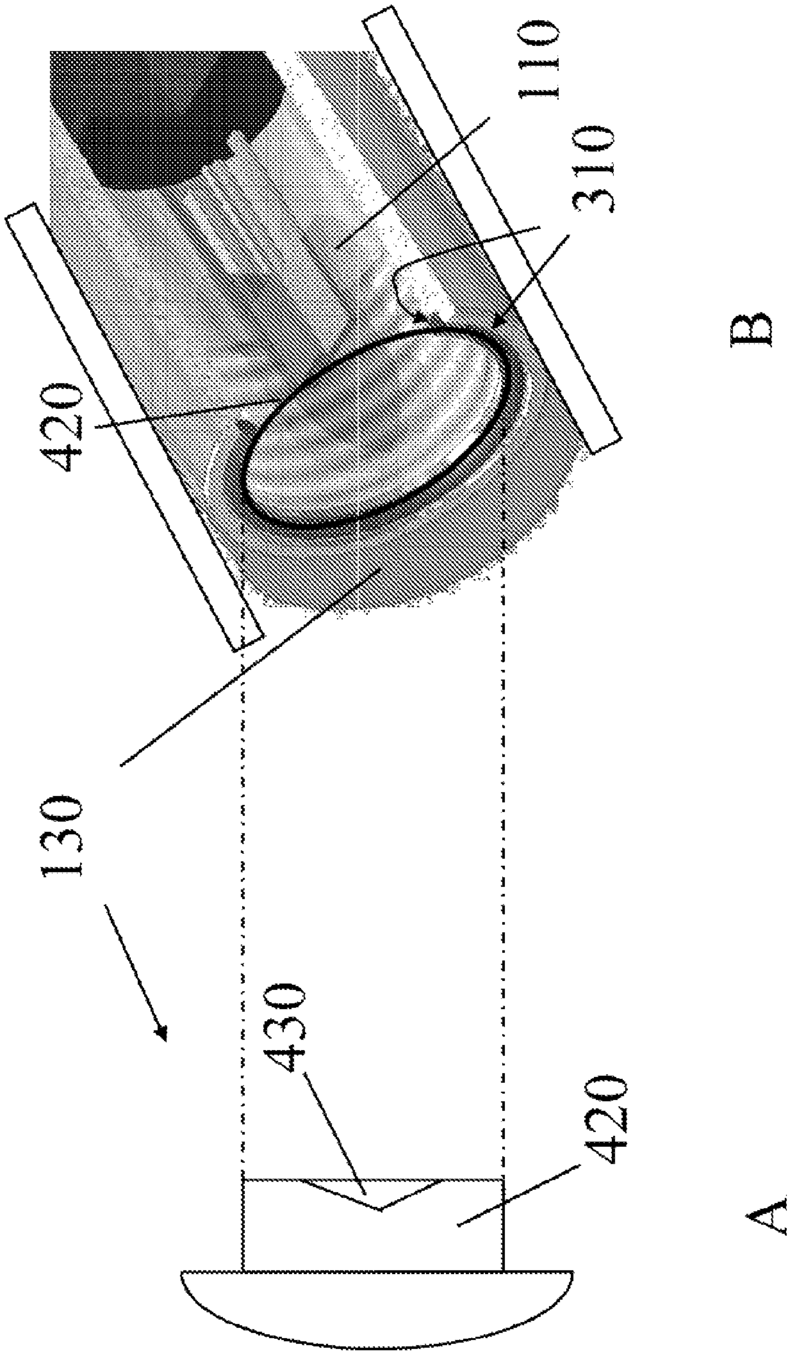
FIGS. 4 (A and B) is a view of the distal end of the DIVA™ of FIG. 1 its end cap.

FIG. 4A shows convex cap 130 of the illustrative embodiment. The cap is mushroom shaped and has a portion 420 which will sealably mate to the interior aperture formed by the cylinder of housing 120. Portion 420 optionally has a recess 430 so as to not impact LED 110, when mated.

FIG. 4B shows the mated cap/o-ring assembly and where portion 420 will sealably mate to the housing 120.

In the illustrative embodiment, as mentioned, housing 120 can be made from stainless steel, the LED 110 is a 1.5v tricolor LED, the vibrating motor 210 is a 1.5 volt DC vibrating motor, cap 130 is a transparent acrylic cap, and a watertight cable gland arrangement (attachable through accessway 220) which prevents water from entering the unit during diving operations, connects either directly to a sensor in the breathing gas; on a device storing the breathing gas, usually in a pressurized state; and/or to electronics controlling and/or monitoring the sensors in the breathing system.

In the illustrative embodiment, the DIVA™ 100 is 2.35 inches long and the housing 120 is machined from 316 Stainless Steel.

The DIVA™ can be deployed in a number of ways, none of which are critical, although some may work better than others. In the illustrative embodiment, the DIYA™ is attached to the Dive Surface Valve DSV (as will be explained in detail below with respect to FIGS. 5-7). In alternative embodiments, the housing may be mounted on a mouth piece that gives the diver access to the breathing gas, such that when the motor is activated, it vibrates the mouthpiece of the diver, which is received by the teeth and skeletal structure of the diver's head amplifying the vibrating alarm and virtually eliminating any possibility that the alarm could not be detected by the diver. Alternatively, the housing can also be mounted on a mask providing a direct alert to the diver's head. In this way, in accordance with a preferred implementation of the present invention, the diver wearing the DIVA™ alarm apparatus feels the tactile/vibration signal stimulating nerve endings in the skin, deep tissue, teeth, and/or skeletal bones, joints, and also hears the tactile signal, as the tactile/vibrating signal also couples into the user's bone structure to stimulate the diver's auditory system (i.e., acoustic energy coupled into the bone structure reaches and stimulates the diver's cochlea).

Figure 5:
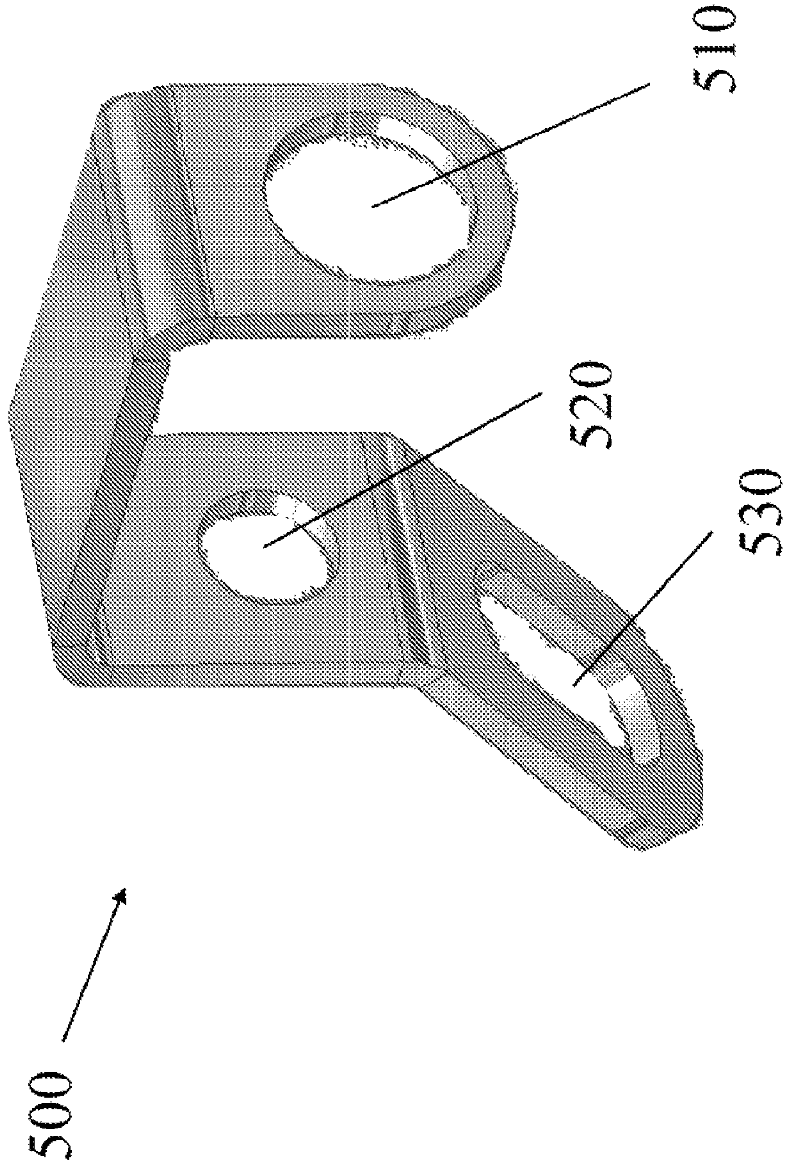
FIG. 5 is an illustrative embodiment of a mounting bracket for mounting the DIVA™ of FIG. 1.
Figure 6:
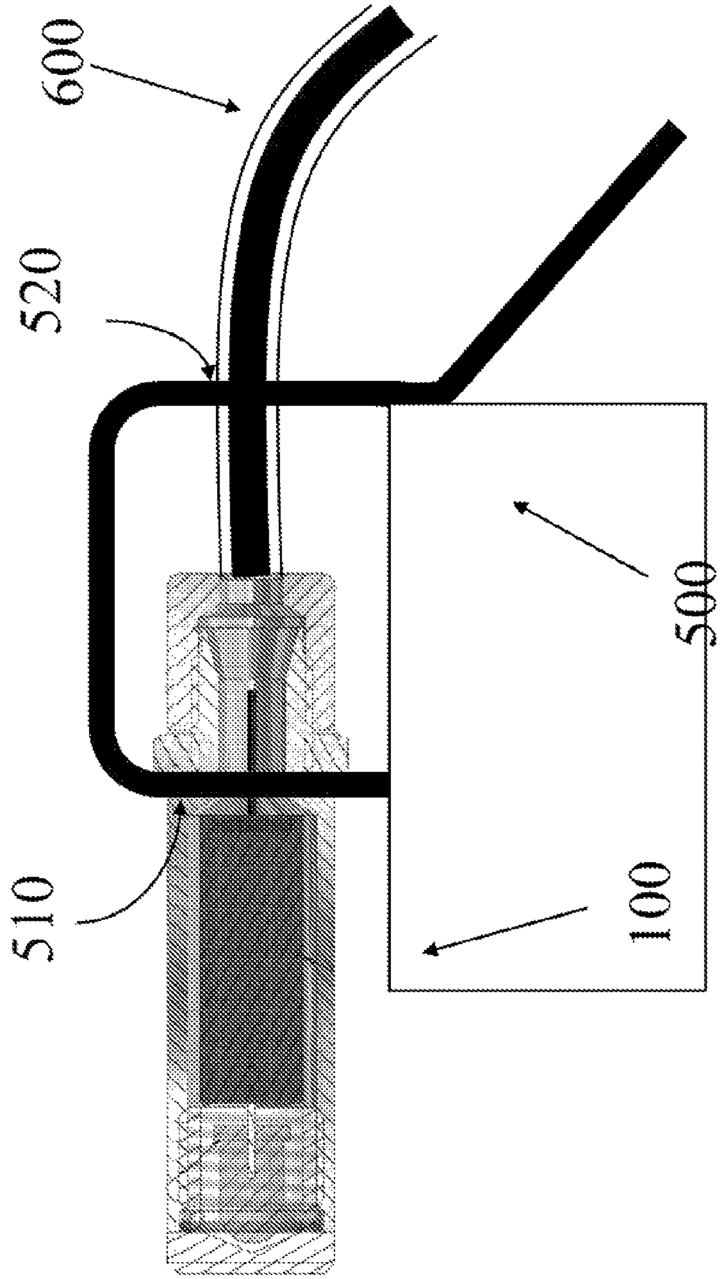
FIG. 6 illustrate a DIVA™ of FIG. 1 mated with the mounting bracket of FIG. 5.
Figure 7:
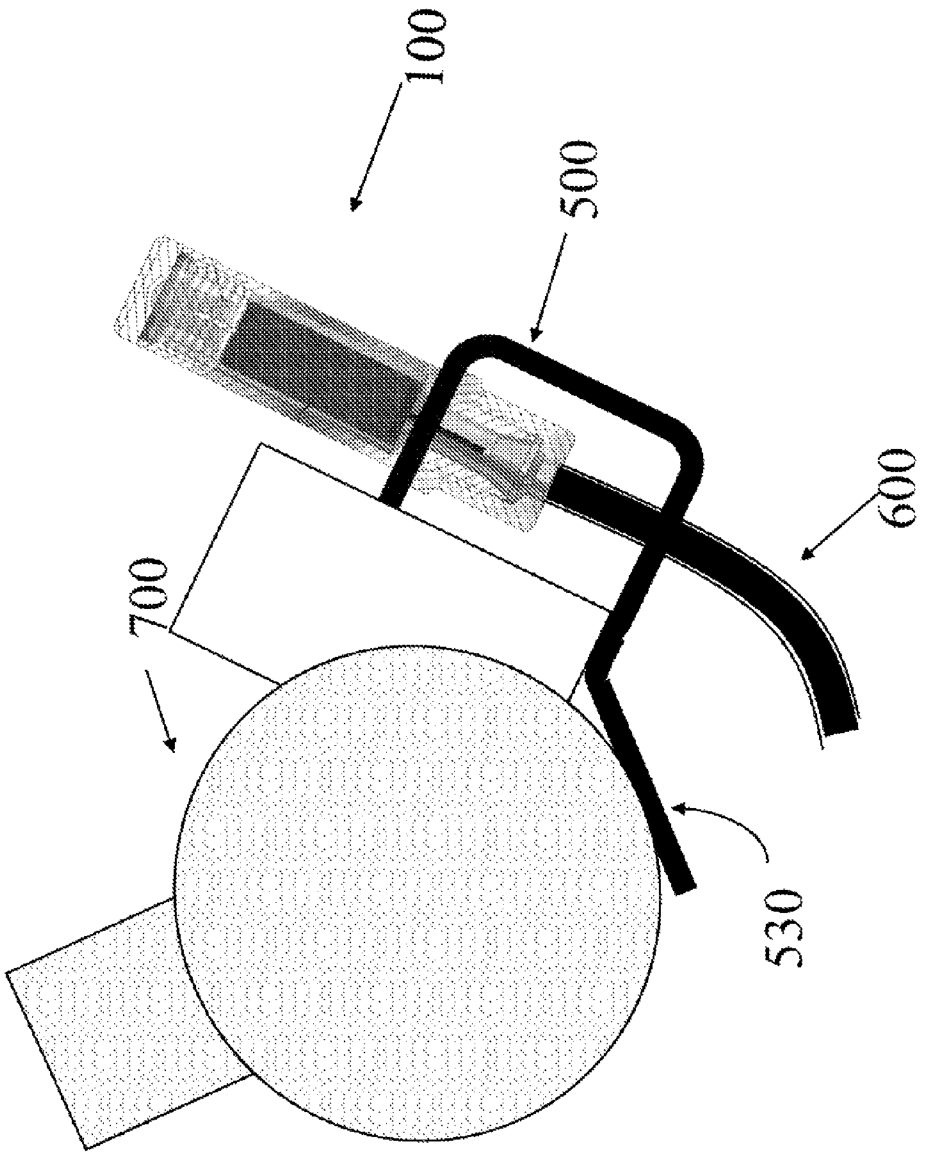
FIG. 7 is an illustrative mounting of the DIVA™/bracket combination of FIG. 6 mounted to a dive surface valve (“DSV”).

With reference to FIGS. 5-7, DIVA™ 100 is mountable via a mount specific bracket. FIG. 5 illustrates a bracket 500 for mounting the DIVA™ 100 to an Inspiration DSV, as the illustrative embodiment. The bracket includes: a mounting aperture 510, through which the DIVA™ is inserted and secured; aperture 520 through which conduit to connect DIVA™ 100 to a dive computer or controller; and slot 530 for mounting to a diver contact surface. FIG. 6 illustrates the DIVA™ 100 attached to bracket 500, with Swagelok end cap 140 securing the DIVA™ 100 through aperture 510 as well as securing cable 600, routed through aperture 520, to DIV ATM 100. FIG. 7 shows the DIVA™ 100 mounted to DSV 700, through slot 530, which allows some adjustment of the height of the DIVA™ (relative to the diver's head) to suit the personal preference of a diver.

An illustrative embodiment of operation of an embodiment of the present invention will now be described. In this illustrative embodiment, the LED indication is programmed so as to flash a different color in a specific code so that the diver is visually made aware of a particular status—e.g., that of the oxygen concentration of the diver's breathing gas. Thus when, e.g., the oxygen content of their breathing gas pass a threshold of life supportability, the LED indicator will provide a visual cue to the diver. Should the diver, through inattention or distraction, not notice or ignore this visual indication, the vibrating motor 210 is activated to provide the cue, thereby alerting the diver to imminent danger.

The illustrative embodiment of the DIV ATM 100 connects to a dive computer or display ("HUD") controller in a configuration with three Oxygen Sensors.

The HUD controller utilizes a pattern of flashes, Red, Green and Orange (a combination of the Red and Green side of the LED flashing at once). Since the HUD is designed (in this embodiment) for the use of three Oxygen Sensors, it will be appreciated that a complete sequence of flashing is comprised of a series of three patterns.

The pattern of flashing is a function of the fraction of a ppO2 (oxygen partial pressure) for each sensor read.

The LED will flash Orange (both Red and Green at the same time) for a ppO2 of 1.0. For every POINT above 1.0 (i.e. 1.1, 1.2, 1.3, etc.) the GREEN LED will flash once. For every POINT BELOW 1.0, the RED LED will flash once.

For example:

If the gas mixture in the loop has a ppO2 of 1.2, the HUD will flash two Greens THREE TIMES (remember, it is responding to all three sensors). It will look to the diver's eye like this:

Green Green-slight pause-Green Green-slight pause-Green Green-longer pause, then a repeat of the same pattern.

Conversely, if the gas mixture in the loop had a ppO2 of 0.8 (two points below 1.0), your HUD will flash two Reds THREE TIMES. It will look like this:

Red Red-slight pause-Red Red-slight pause-Red Red

The exemplary coding of the LED signals is as follows:

| PARTIAL PRESSURE OF OXYGEN (1.0 AND ABOVE) | LED FLASHES |
|---|---|
| 1.0 | 1 ORANGE (FOR EACH SENSOR) |
| 1.1 | 1 GREEN |
| 1.2 | 2 GREEN |
| 1.3 | 3 GREEN |
| 1.4 | 4 GREEN |
| 1.5 | 5 GREEN |
| 1.6 | 6 GREEN |
| 1.7 | 7 GREEN |
| 1.8 AND ABOVE | SOLID GREEN |

| PARTIAL PRESSURE OF OXYGEN (1.0 AND BELOW) | LED FLASHES |
|---|---|
| 1.0 | 1 ORANGE (FOR EACH SENSOR) |
| .9 | 1 RED |
| .8 | 2 RED |
| .7 | 3 RED |
| .6 | 4 RED |
| .5 | 5 RED |
| .4 | 6 RED |
| .3 AND BELOW | 7 RED |

The present invention has been illustrated and described with reference to particular embodiments and applications thereof. It will be readily apparent to those skilled in that art that the present invention will have applications beyond those described herein for purposes of description of the invention. For example, the present invention can be adapted for use in any environment where flexible structure formation is desired by implementing the principals taught herein.

To facilitate discussion of the present invention, a preferred embodiment is assumed, however, the above-described embodiments are merely illustrative of the principals of the invention and are not intended to be exclusive embodiments thereof. It should be understood by one skilled in the art that alternative embodiments drawn to variations in the enumerated embodiments and teachings disclosed herein can be derived and implemented to realize the various benefits of the present invention. By way of example, it is understood that although the embodiments have been described with respect to specific configurations, in practice, and also depending on the application, different configurations may be allowed and/or certain other configurations may be desired.

By way of more specific illustrative examples, those skilled in the art will understand in view of the foregoing illustrative embodiments that the DIVA™ enclosure may include power supply and or control circuitry for energizing and/or controlling the vibration generator and/or LEDs in response to a signal provided via conduit 600. Such control circuitry may be provided to also decode a signal provided via conduit 600, wherein such signal may be encoded to specify different alarm conditions, etc. Alternatively, the DIVA™ enclosure may not include such control and/or power supply circuitry, and all signaling for energizing and/or controlling the LEDs and vibration generator would be provided via conduit 600. Alternatively, such power supply and/or control circuit functionality may be partitioned between components internal and external to the DIVA™. Additionally, as may be appreciated, in various implementations, conduit 600 may be implemented to include one or more electrical conductors (e.g., wires), and additionally or alternatively, one or more signals may be provided by, for example, an optical or pressure signal provided via conduit 600.

Additionally, with respect to signaling provided to the DIVA™, those skilled in the art understand that such signaling may include signaling related to the user's/diver's condition and/or environment. Further, such signaling may represent any data included within the dive computer, such as dive table time limits, dive time duration, depth limits, air supply limits, direction, distance, water temperature, assent rates, heart rate, breathing rate, etc.

Accordingly, it should further be understood, therefore, that the foregoing and many various modifications, omissions and additions may be devised by one skilled in the art without departing from the spirit and scope of the invention. It is therefore intended that the present invention is not limited to the disclosed embodiments but should be defined in accordance with the claims which follow.

Finally, it is further noted that while the system described and shown hereinabove in accordance with the present invention provide many useful features and advantages, the geometric designs and shapes of each of the individual components, as depicted in the various drawings, represent ornamental designs that may be subject to separate protection thereof.

What is claimed is:

1. An alarm apparatus for use with a breathing apparatus that provides a source of breathing gas to a user, said alarm apparatus comprising: a tactile signal generator that is mechanically coupled to a mouthpiece of the breathing apparatus and that is selectively energized in response to a first signal representing at least one parameter corresponding to the breathing apparatus status to generate a tactile signal that, in the event that the mouthpiece is in the mouth of the user, (i) is capable of being felt by the user via the mouthpiece, and (ii) couples via the mouthpiece into the bone structure of the user to stimulate the user's auditory system via the user's bone structure such that the tactile signal is heard by the user.

2. The alarm apparatus according to claim 1, wherein the tactile signal is a vibration.

3. The alarm apparatus according to claim 2, wherein the vibration is generated by a motor that rotates an eccentric weight.

4. The alarm apparatus according to claim 1, wherein the at least one parameter includes at least one status condition for the breathing gas.

5. The alarm apparatus according to claim 4, wherein the at least one parameter includes at least one of an amount, level, and partial pressure of at least one component in the breathing gas.

6. The alarm apparatus according to claim 4, wherein the at least one parameter includes at least one of an amount, level, and pressure of gas in tanks or containers supplying the breathing gas to the user.

7. The alarm apparatus according to claim 1, further comprising at least one light emitting device responsive to a second signal representing at least one parameter corresponding to the breathing apparatus status.

8. The alarm apparatus according to claim 7, wherein said first and second signals are the same signal representing at least one parameter corresponding to the breathing apparatus.

9. The alarm apparatus according to claim 7, wherein the light emitting device and the tactile signal generator are both energized at substantially the same time to provide a visual signal and a tactile signal to the user.

10. The alarm apparatus according to claim 7, wherein the tactile signal generator is energized at a time delay after said light emitting device is energized in the event that the light emitting device remains energized for a predetermined period of time.

11. The alarm apparatus according to claim 7, wherein the at least one light emitting device comprises a red light emitting diode (LED) and a green LED.

12. The alarm apparatus according to claim 11, wherein the LEDs are selectively energized individually or together in response to said second signal to selectively provide one of a red, yellow, and orange light signal depending on said second signal.

13. The alarm apparatus according to claim 7, further comprising an environmentally-sealed housing having an interior cavity in which said light emitting device and said tactile signal generator are disposed.

14. The alarm apparatus according to claim 1, wherein said first signal is coupled to the output of at least one sensor.

15. The alarm apparatus according to claim 1, wherein said first signal is provided by a dive computer and corresponds to dive computer data.

16. The alarm apparatus according to claim 1, further comprising: an elongated housing having an interior cavity and a proximal and a distal end, each end having an opening to said interior cavity, wherein said tactile signal generator is mounted to said housing and disposed within said interior cavity toward said distal end and comprises a motor that rotates an eccentric weight; an optical window sealably mounted to enclose, and provide a water-tight seal of, the proximal opening; at least one light emitting device disposed within said interior cavity toward said proximal end, said at least one light emitting device being selectively energized in response to a second signal representing at least one parameter corresponding to the breathing apparatus status, such that the at least one light emitting device selectively emits light that passes through said optical window; and a water-tight sealable fitting cooperative with the distal end to sealably enclose the distal end opening and sealably couple a conduit into said interior cavity from the exterior of said elongated housing, wherein said first and second signals are coupled via said conduit.

17. The alarm apparatus according to claim 16, wherein said optical window is formed as a lens to guide the light emitted by said at least one light emitting device.

18. The alarm apparatus according to claim 16, wherein said first and second signals are the same signal representing at least one parameter corresponding to the breathing apparatus.

19. The alarm apparatus according to claim 1, wherein the tactile signal is modulated to encode information representing one or more of said at least one parameter.

20. The alarm apparatus according to claim 19, wherein the tactile signal is modulated according to at least one of frequency, intensity, duration, repetition frequency, and pattern.

21. The alarm apparatus according to claim 19, wherein the tactile signal is modulated according to different ones of said at least one parameter.

22. The alarm apparatus according to claim 19, wherein the tactile signal is modulated to encode quantitative information about at least one of said at least one parameter.

23. An alarm apparatus for use with a breathing apparatus that provides a source of breathing gas to a user, said alarm apparatus comprising:

a housing that is capable of being mechanically coupled to a mouthpiece of the breathing apparatus;

means for coupling at least one signal representing at least one parameter corresponding to the breathing apparatus status into said housing; and means, disposed within said housing, for generating a tactile signal in response to at least one of said at least one signal representing at least one parameter corresponding to the breathing apparatus status, wherein, in the event that said mouthpiece is in the mouth of the user, said tactile signal (i) is capable of being felt by the user via the mouthpiece, and (ii) is coupled via the mouthpiece into the bone structure of the user to stimulate the user's auditory system via the user's bone structure such that the tactile signal is heard by the user.

24. The alarm apparatus according to claim 23, further comprising means for emitting a light signal in response to one or more of said at least one signal.

25. The alarm apparatus according to claim 23, wherein the tactile signal is modulated to encode information representing one or more of said at least one parameter.

26. The alarm apparatus according to claim 23, further comprising means for attaching the alarm apparatus to the mouthpiece of the breathing apparatus.

27. A method of alerting a user of a breathing apparatus having a mouthpiece, comprising:

generating a vibration signal in response to a signal representing at least one parameter corresponding to the breathing apparatus status; and coupling the vibration signal into said mouthpiece such that, in the event that said mouthpiece is in the mouth of said user, the vibration signal (i) is felt by the user via the mouthpiece, and (ii) is coupled via the mouthpiece into the bone structure of the user to stimulate the user's auditory system via the user's bone structure such that the user hears the vibration signal.

28. The method according to claim 27, wherein the vibration signal stimulates the user's cochlea.

29. The method according to claim 27, wherein the vibration signal is coupled to a mask worn on the head of the user.

30. The method according to claim 27, wherein the vibration signal is generated by a component that is attached to the mouthpiece of the user.

* * * * *